United States Patent
Botelho

(10) Patent No.: US 9,638,675 B2
(45) Date of Patent: May 2, 2017

(54) GAS CHROMATOGRAPHY OVEN AND SYSTEMS AND METHODS INCLUDING SAME

(71) Applicant: PerkinElmer Health Sciences, Inc., Waltham, MA (US)

(72) Inventor: James E. Botelho, Danbury, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 181 days.

(21) Appl. No.: 14/572,847

(22) Filed: Dec. 17, 2014

(65) Prior Publication Data
US 2015/0196866 A1 Jul. 16, 2015

Related U.S. Application Data

(60) Provisional application No. 61/928,161, filed on Jan. 16, 2014.

(51) Int. Cl.
*G01N 30/30* (2006.01)
*G01N 30/02* (2006.01)

(52) U.S. Cl.
CPC ....... *G01N 30/30* (2013.01); *G01N 2030/025* (2013.01); *G01N 2030/3084* (2013.01)

(58) Field of Classification Search
CPC ........... G01N 30/30; G01N 2030/3084; G01N 2030/025
See application file for complete search history.

(56) References Cited

U.S. PATENT DOCUMENTS

| 3,422,603 | A | * | 1/1969 | Redmond, Jr. | ........ | G01N 30/30 219/400 |
| 4,070,169 | A | * | 1/1978 | Iwao | ....................... | B01D 15/08 219/400 |
| 4,181,613 | A | * | 1/1980 | Welsh | .................... | B01D 15/08 210/179 |
| 4,286,456 | A | * | 9/1981 | Sisti | ..................... | B01D 53/025 219/201 |

(Continued)

OTHER PUBLICATIONS

Notification Concerning Transmittal of International Preliminary Report on Patentability in corresponding PCT Application No. PCT/US2014/071883, mailed Jul. 28, 2016 (9 pages).

(Continued)

*Primary Examiner* — Robert Clemente
(74) *Attorney, Agent, or Firm* — Myers Bigel, P.A.

(57) ABSTRACT

A gas chromatography system includes a gas chromatography oven and a gas chromatography column. The gas chromatography oven includes a housing and a flow generating system. The housing defines an oven chamber and an intake port fluidly communicating with the oven chamber. The fluid flow generating system includes a radial flow impeller. The gas chromatography column is disposed in the oven chamber. The oven is configured to selectively operate in each of: a cooling mode wherein the radial flow impeller generates a cooling fluid flow that is drawn from the intake port and flows about the column and out of the oven chamber; and alternatively, a recirculating mode wherein the radial flow impeller generates a recirculating fluid flow within the oven chamber that repeatedly flows about the column and back to the radial flow impeller.

15 Claims, 13 Drawing Sheets

(56) References Cited

U.S. PATENT DOCUMENTS

| | | | | |
|---|---|---|---|---|
| 4,420,679 A | * | 12/1983 | Howe | F24C 15/325 126/21 A |
| 4,599,169 A | * | 7/1986 | Ray | G01N 30/30 210/175 |
| 4,771,628 A | * | 9/1988 | Sisti | G01N 30/30 73/23.25 |
| 5,497,760 A | | 3/1996 | Alden et al. | |
| 5,807,426 A | * | 9/1998 | Ohtsuki | G01N 30/30 73/23.25 |
| 5,942,675 A | * | 8/1999 | Wilson | G01N 30/30 73/23.35 |
| 5,979,221 A | * | 11/1999 | Walte | G01N 30/30 73/23.25 |
| 6,248,158 B1 | * | 6/2001 | Abdel-Rahman | G01N 30/30 210/198.2 |
| 6,485,543 B1 | * | 11/2002 | MacDonald | G01N 30/30 95/87 |
| 7,984,638 B2 | | 7/2011 | White | |
| 2003/0037592 A1 | | 2/2003 | D'Couto et al. | |
| 2005/0258088 A1 | | 11/2005 | Botelho et al. | |
| 2008/0047323 A1 | | 2/2008 | Botelho et al. | |
| 2008/0105033 A1 | | 5/2008 | Tipler et al. | |
| 2009/0223369 A1 | * | 9/2009 | Uegaki | F27D 21/0028 96/102 |
| 2012/0199108 A1 | | 8/2012 | Wasson et al. | |
| 2012/0285325 A1 | | 11/2012 | Tipler et al. | |

OTHER PUBLICATIONS

Notification of Transmittal of the International Search Report and the Written Opinion of the International Searching Authority, or the Declaration, in corresponding PCT Application No. PCT/US2014/071883, mailed Apr. 10, 2015 (11 pages).

Electric Trading Co. "Blower Wheels", http://www.blowerwheel.com/blower-wheels.htm; printed Jul. 19, 2013; 3 pages.

Electric Trading Co. "Blower Wheel Double Inlet Class-2 Heavy Duty", http://www.blowerwheel.com/blower-wheel-di-hd.htm; printed Jul. 19, 2013; 4 pages.

Electric Trading Co. "Blower Wheel Backward Incline Non-Overloading", http://www.blowerwheel.com/blower-wheel-bc.htm; printed Jul. 19, 2013; 2 pages.

* cited by examiner

GAS CHROMATOGRAPHY OVEN AND SYSTEMS AND METHODS INCLUDING SAME

RELATED APPLICATION(S)

The present application claims the benefit of and priority from U.S. Provisional Patent Application No. 61/928,161, filed Jan. 16, 2014, the entirety of which is incorporated by reference herein.

FIELD

The present technology relates to gas chromatography and, more particularly, to gas chromatography ovens.

BACKGROUND

Gas chromatography is commonly used in analytic chemistry for separating and analyzing compounds of a sample. For example, a gas chromatograph may be used to test the purity of a sample, identify a compound, separate different components of a mixture or to prepare (e.g., purify) compounds from a mixture.

SUMMARY

According to embodiments of the present technology, a gas chromatography system includes a gas chromatography oven and a gas chromatography column. The gas chromatography oven includes a housing and a flow generating system. The housing defines an oven chamber and an intake port fluidly communicating with the oven chamber. The fluid flow generating system includes a radial flow impeller. The gas chromatography column is disposed in the oven chamber. The oven is configured to selectively operate in each of: a cooling mode wherein the radial flow impeller generates a cooling fluid flow that is drawn from the intake port and flows about the column and out of the oven chamber; and alternatively, a recirculating mode wherein the radial flow impeller generates a recirculating fluid flow within the oven chamber that repeatedly flows about the column and back to the radial flow impeller.

In some embodiments, the oven includes a heating element, and in the recirculating mode, the recirculating fluid flow flows about the heating element and is heated thereby.

In some embodiments, the oven includes an exhaust port, and, in the cooling mode, the cooling fluid flow flows out of the housing through the exhaust port.

According to some embodiments, the oven includes at least one baffle in the oven chamber defining an exit channel and a return channel. The cooling fluid flow flows through the exit channel to the exhaust port, and the recirculating fluid flow flows through the return channel to the radial flow impeller. In some embodiments, the oven includes a closure mechanism to selectively open and close the intake port, the oven operates in the cooling mode when the intake port is open, and the oven operates in the recirculating mode when the intake port is closed.

According to some embodiments, the radial flow impeller has first and second opposed axial inlets, the cooling fluid flow is drawn into the radial flow impeller through the first axial inlet in the cooling mode, and the recirculating fluid flow is drawn into the radial flow impeller through the second axial inlet in the recirculating mode.

In some embodiments, in each of the cooling mode and the recirculating mode, the radial flow impeller discharges a forced fluid flow radially outwardly therefrom, the column is configured in a substantially circular column loop, and the radial flow impeller is located within the column loop so that the forced fluid flow is directed toward the column. The forced fluid flow may be substantially uniformly distributed about the full circumference of the radial flow impeller. In some embodiments, the radial flow impeller rotates about an impeller axis, and the column loop is centered about a column axis substantially concentric with the impeller axis and defines a column loop plane substantially perpendicular to the impeller axis.

The radial flow impeller may include a plurality of backward inclined blades. In some embodiments, the blades are convexly curved.

In some embodiments, the radial flow impeller rotates about an impeller axis and includes a plurality of blades, and each of the blades extends substantially parallel to the impeller axis across its full width.

According to some embodiments, the cooling fluid flow is drawn from ambient air through the intake port when the gas chromatography system is in the cooling mode.

The cooling fluid flow and the recirculating fluid flow may each be air flows.

According to further embodiments of the technology, a gas chromatography system includes a gas chromatography oven and a gas chromatography column. The gas chromatography oven includes a housing defining an oven chamber, and a fluid flow generating system including a radial flow impeller and operable to drive the radial flow impeller such that the radial flow impeller discharges a forced fluid flow radially outwardly from the radial flow impeller. The gas chromatography column is disposed in the oven chamber. The column is configured in a substantially circular column loop. The radial flow impeller is located within the column loop so that the forced fluid flow is directed toward the column.

The forced fluid flow may be substantially uniformly distributed about the full circumference of the radial flow impeller. The radial flow impeller rotates about an impeller axis, and the column loop is centered about a column axis substantially concentric with the impeller axis and defines a column loop plane substantially perpendicular to the impeller axis.

In some embodiments, the forced fluid flow is an air flow.

According to further embodiments of the technology, a gas chromatography system includes a gas chromatography oven and a gas chromatography column. The gas chromatography oven includes a housing defining an oven chamber, and a fluid flow generating system including a fluid distributing device and operable to discharge a forced fluid flow radially outwardly from the fluid distributing device. The gas chromatography column is disposed in the oven chamber. The column is configured in a substantially circular column loop. The fluid distributing device is located within the column loop so that the forced fluid flow is directed toward the column. The forced fluid flow is substantially uniformly distributed about the full circumference of the fluid distributing device.

The forced fluid flow can be an air flow.

Further features, advantages and details of the present technology will be appreciated by those of ordinary skill in the art from a reading of the figures and the detailed description of the preferred embodiments that follow, such description being merely illustrative of the present technology.

DETAILED DESCRIPTION

Figure 1:
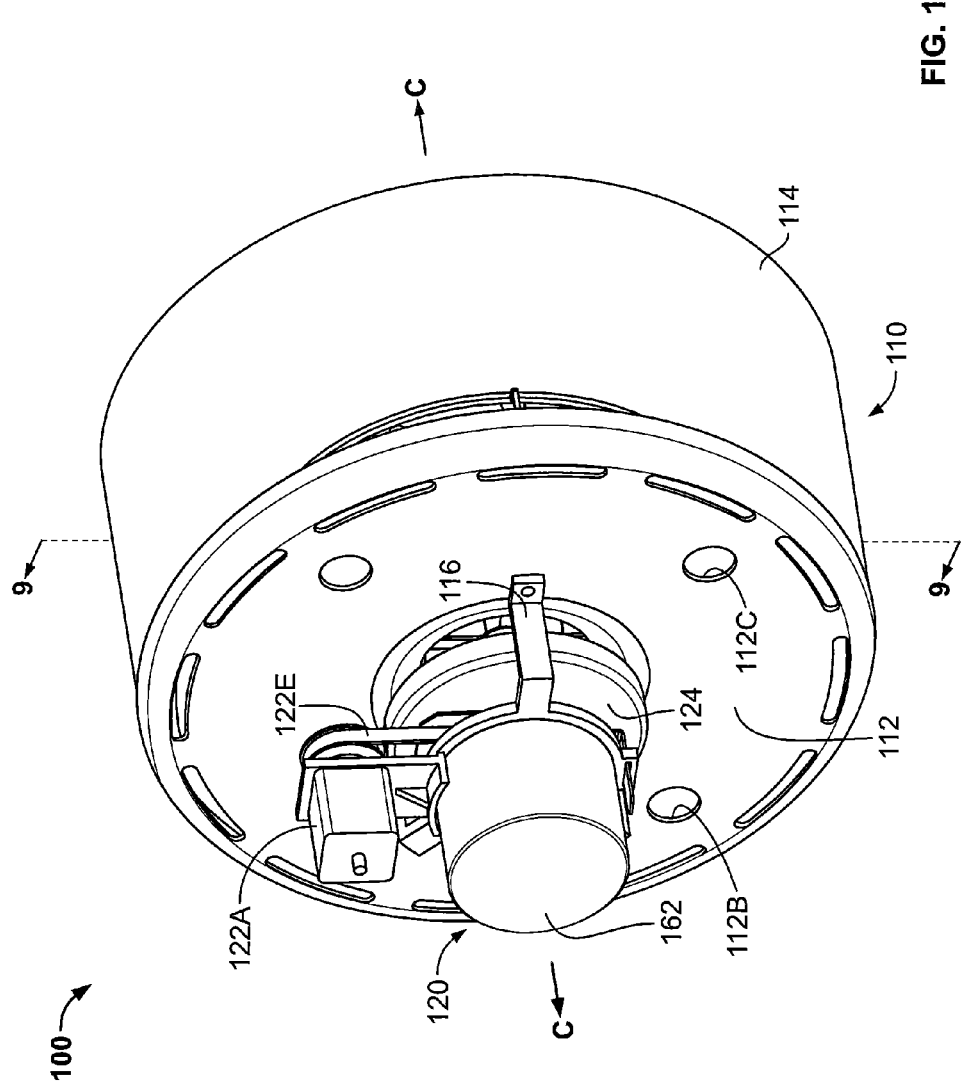
FIG. 1 is a front perspective view of a gas chromatography (GC) oven according to embodiments of the technology.

The present technology now will be described more fully hereinafter with reference to the accompanying drawings, in which illustrative embodiments of the technology are shown. In the drawings, the relative sizes of regions or features may be exaggerated for clarity. This technology may, however, be embodied in many different forms and should not be construed as limited to the embodiments set forth herein; rather, these embodiments are provided so that this disclosure will be thorough and complete, and will fully convey the scope of the technology to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present technology.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

With reference to the figures, a gas chromatography (GC) system 10 (FIG. 12) according to some embodiments of the technology is schematically shown therein. The GC system 10 includes a gas chromatograph air bath, forced convection heating oven 100 (FIGS. 1-11) according to embodiments of the technology and as described in more detail herein below. With reference to FIG. 12, the GC system 10 further includes a carrier gas supply 20, a feed line 22, a flow controller or regulator 24 in the feed line 22, a column inlet or sample injector 26, a column tubing 30, a detector 40, a recorder 42, and a controller 50. The various components and architecture of the GC system 10 may be modified as desired and a GC oven as disclosed herein may be incorporated into any suitable GC system.

Exemplary operation of the GC system 10 will now be described with the exception of the more particular operation of the GC oven 100. The carrier gas supply 20 provides a continuous, pressurized flow of a selected carrier gas (the mobile phase) via the feed line 22 to an inlet of the column 30. The flow rate of the supplied carrier gas can be controlled using the flow controller 24. The sample injector 26 introduces the sample into the continuous flow of the carrier gas. The carrier gas sweeps the sample through the column 30 to the detector 40, and thereafter to waste collection, a further detector or other desired destination. The oven 100 selectively heats the column 30 before, during and/or after the sample is passed therethrough in order to control the temperature of the column 30 and the sample. The column 30 includes an inner layer or packing of a selected stationary phase 31B (FIG. 4) in or on the inner wall of the bore 31A of the column 30. The gaseous compounds of the sample interact with the stationary phase; having a different affinity for each component, retains the different components of the sample for different times. As a result, the different compounds elute at different times and take different amounts of time to pass through and exit the column 30 to the detector 40 (i.e., the components have different retention times within the column 30). The detector 40 monitors the outlet stream from the column 30 to detect or sense the time at which each analyte component emerges from the column 30 and reaches the detector 40, and/or the amount of the analyte. The detection data from the detector 40 is stored by the recorder 42. Various parameters of the process may be controlled by the controller 50, including the carrier gas flow rate (using the flow controller 24), the column and/or mobile phase temperatures (using the GC oven 100), and the sample injection timing and rate (using the sample injector 26).

According to some embodiments, the GC oven 100 heats or cools (with applied liquid cryogen) the column 30 to a temperature in the range of from about 100° C. to 450° C.

The carrier gas may be any suitable gas. The carrier gas may include helium, nitrogen, hydrogen or argon, for example.

The sample injector 26 may be a manual injector or an auto sampler, for example.

Figure 2:
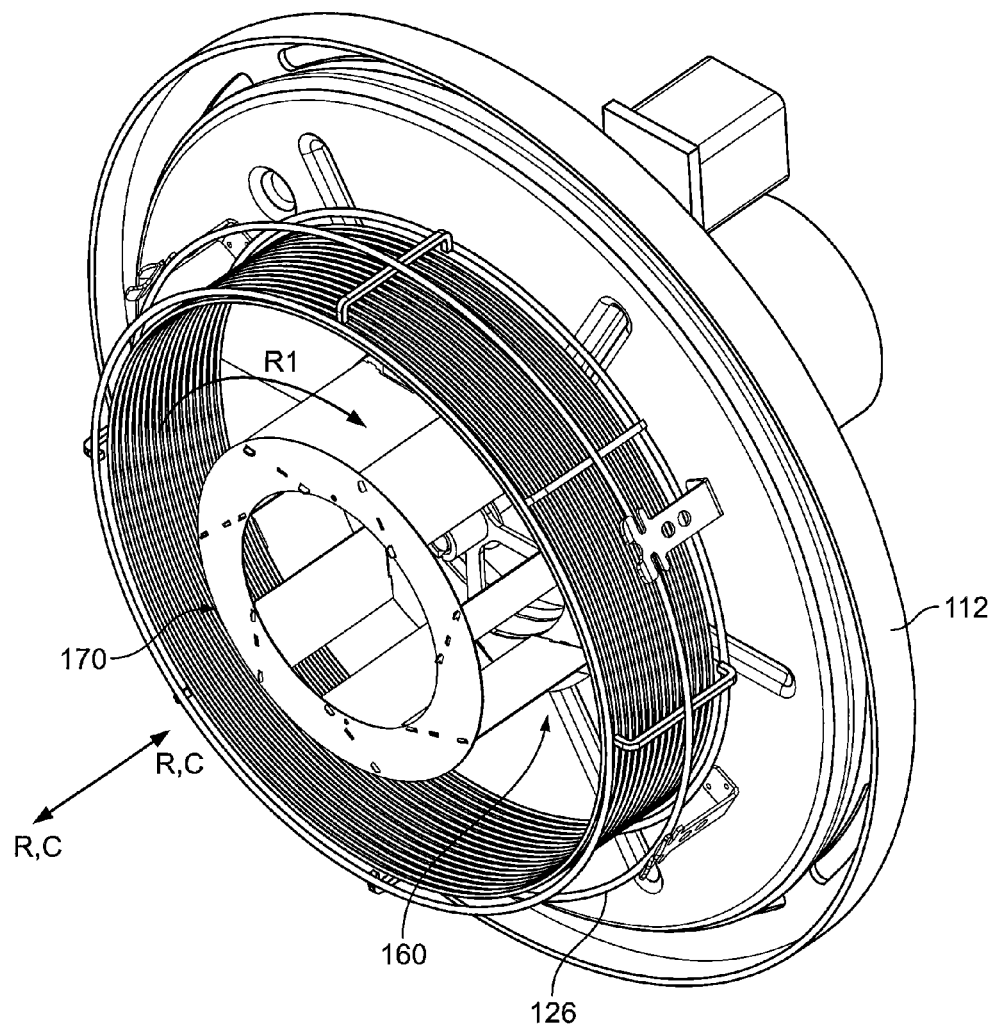
FIG. 2 is a rear perspective view of a lid assembly forming a part of the GC oven of FIG. 1.
Figure 9:
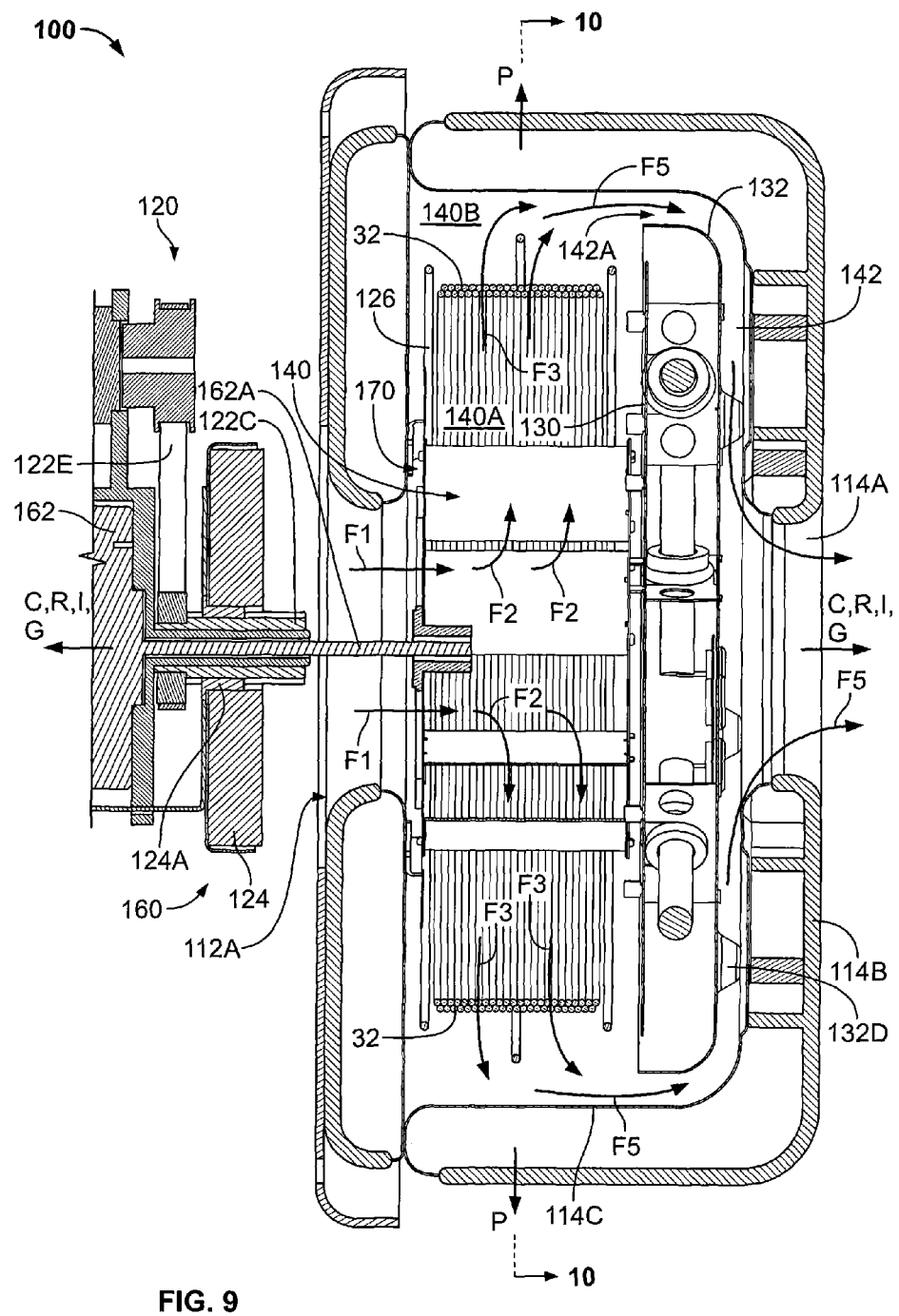
FIG. 9 is a fragmentary, cross-sectional view of the GC oven of FIG. 1 taken along the line 9-9 of FIG. 1, wherein the GC oven is operating in a cooling mode.

The column 30 may be wound or coiled into a coil 32 generally centered about a coil axis C-C (FIGS. 2 and 9). The column 30 may be formed of any suitable material. In some embodiments, the column 30 is formed of fused silica or other glass. In some embodiments, the column 30 is formed of metal. In some embodiments, the column 30 is capillary tubing (e.g., glass capillary tubing). In some embodiments, the column 30 is packed or coated in its interior bore with the stationary phase. According to some embodiments, the column 30 has a bore inner diameter in the range of from about 50 μm to 1500 μm and, in some embodiments, from about 250 μm to 530 μm.

The detector 40 may be any suitable detector. Multiple detectors may be provided to monitor the gas stream. Suitable detectors may include, for example, a flame ionization detector (FID), a thermal conductivity detector (TCD), an electron capture detector (ECD), a nitrogen-phosphorous detector (NPD), a flame photometric detector (FPD), a photoionization detector (PID) and a mass spectrometer (MS).

The controller 50 may be any suitable device for providing the functionality described herein. According to some embodiments, the controller 50 is a microprocessor-based computer.

Turning to the GC oven 100 in more detail, the GC oven 100 has an oven central axis C-C (FIGS. 1 and 9) and includes a housing 110, a closure mechanism 120, a column loom or support frame 126, a heating element 128, a front baffle 130, a rear baffle 132, and a fluid flow generating system 160. The housing 110 defines a cylindrical column chamber 140 and an inlet port 112A and an exhaust port 114A fluidly communicating with the chamber 140.

Figure 7:
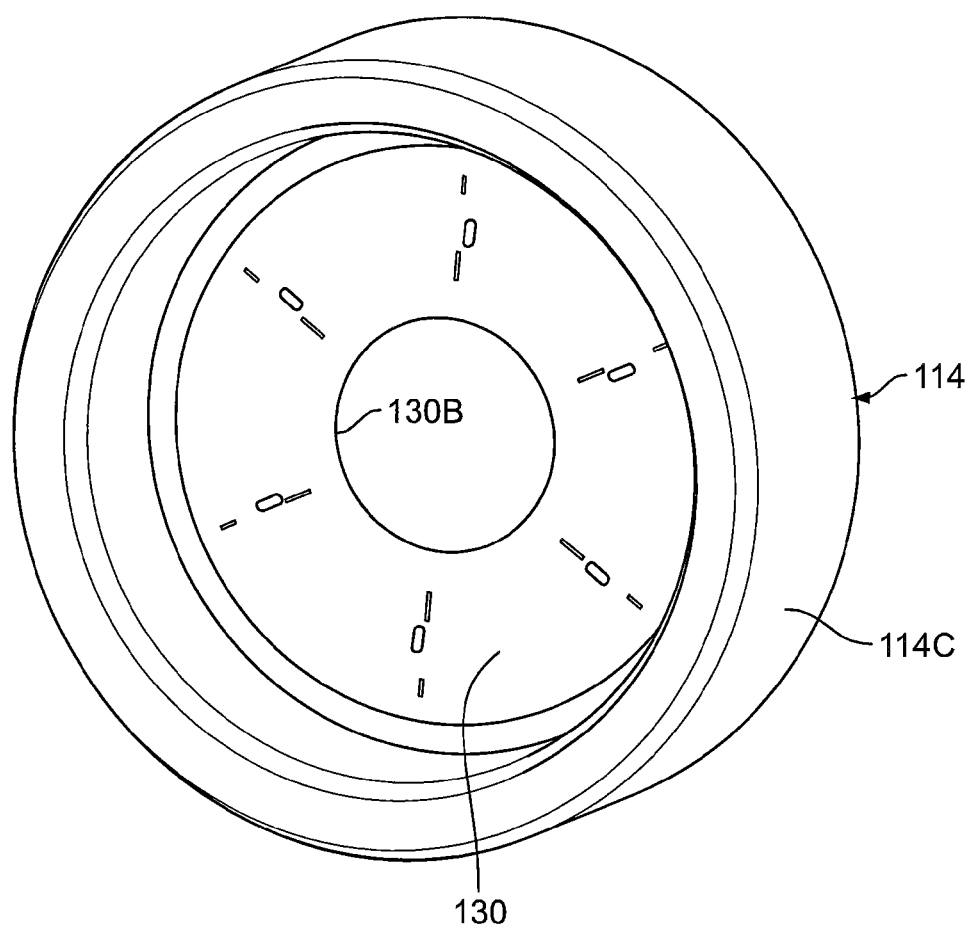
FIG. 7 is a front perspective view of a base assembly forming a part of the GC oven of FIG. 1.
Figure 8:
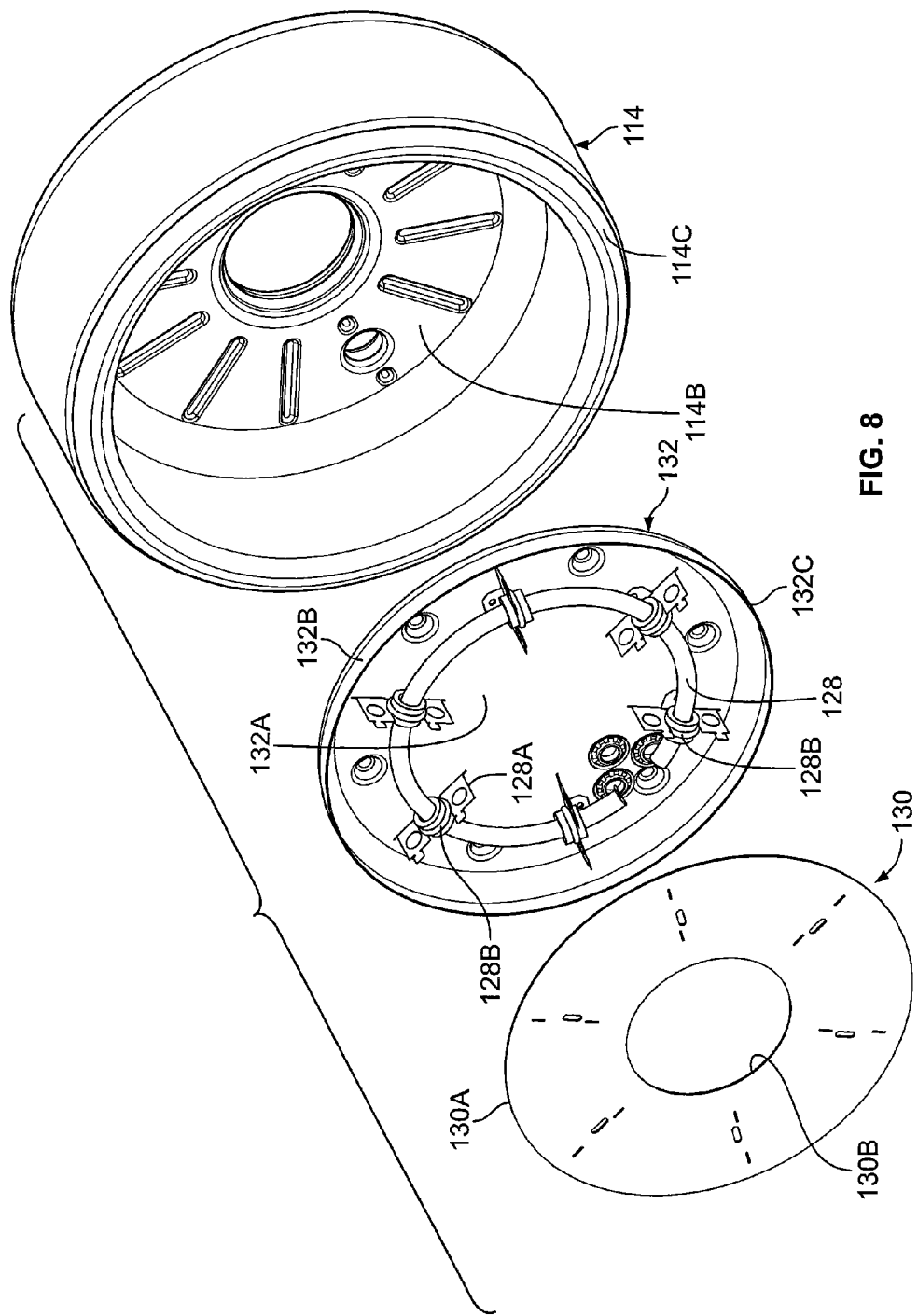
FIG. 8 is an exploded, front perspective view of the base assembly of FIG. 7.

The housing 110 includes a lid 112 (FIGS. 2 and 3) and a base 114 (FIGS. 7 and 8). The inlet port 112A, a column entrance opening 112B and a column exit opening 112C are defined in the lid 112. The base 114 includes a rear end wall 114B and an annular side wall 114C. The exhaust port 114A is defined in the end wall 114B. One or more support brackets 116 are secured to the lid 112. The lid 112 may be removable from the base 114 to permit convenient access to the chamber 140. The lid 112 and the base 114 may be formed of any suitable material(s) and may be thermally insulating.

The closure mechanism 120 (FIGS. 1, 3 and 9) includes a door 124 and a threaded bore 124A defined in the door 124. A motor 122A is mounted on the lid 112 by the brackets 116. The motor 122A is operable to rotate a pulley and thereby, via a chain or belt 122E, rotate a threaded lead screw or collar 122C in the bore 124A. In this manner, the motor 122A can be used to drive the door 124 toward and away from the inlet port 112A depending on the direction of the rotation.

The column frame 126 (FIG. 3) may include a plurality of wires or wire segments 126A forming a cylindrical loop. Radial openings 126B are defined in the loop so that the vast majority of the frame 126 is open for flow through of air.

A coiled section or loop 32 (FIGS. 3 and 4) of the column 30 is disposed in the chamber 140 and mounted on the frame 126. A feed end section 34 and an exit end section 36 of the column extend out of the chamber 140 and the housing 110 through the openings 112B and 112C (FIG. 1). According to some embodiments, the column loop 32 includes or consists of a plurality of looped column sections 32A defining voids 32B therethrough (FIG. 4) so that the loop 32 is radially porous. The column sections 32A may be overlapped or radially stacked at locations about the circumference of the loop 32. The column sections 32A may be woven together, loosely bound by a thread or threads, and/or tied to the frame 126. In some embodiments, the column loop 32 is substantially cylindrical. In some embodiments, the width W (FIG. 11) of the loop 32 is in the range of from about 2 cm to 10 cm.

The heating element 128 (FIG. 8) may be configured as an annular, and in some embodiments circular, loop and is mounted on and between the baffles 130, 132 by brackets 128A and thermally insulating spacers 128B. The heating element 128 may be any suitable device for controllably generating heat. In some embodiments, the heating element 128 is an electrically sensitive heating element (e.g., a nichrome wire).

The front baffle 130 (FIG. 8) is a relatively flat disc including a central return opening 130B defined therein and having a free outer, peripheral terminal edge 130A. The rear baffle 132 includes a flat body section 132A, an annular upstanding lip or sidewall 132B terminating in a free peripheral edge 132C, and standoffs 132D. The baffles 130, 132 may be formed of any suitable materials and, in some embodiments, are formed of a metal such as stainless steel.

Figure 10:
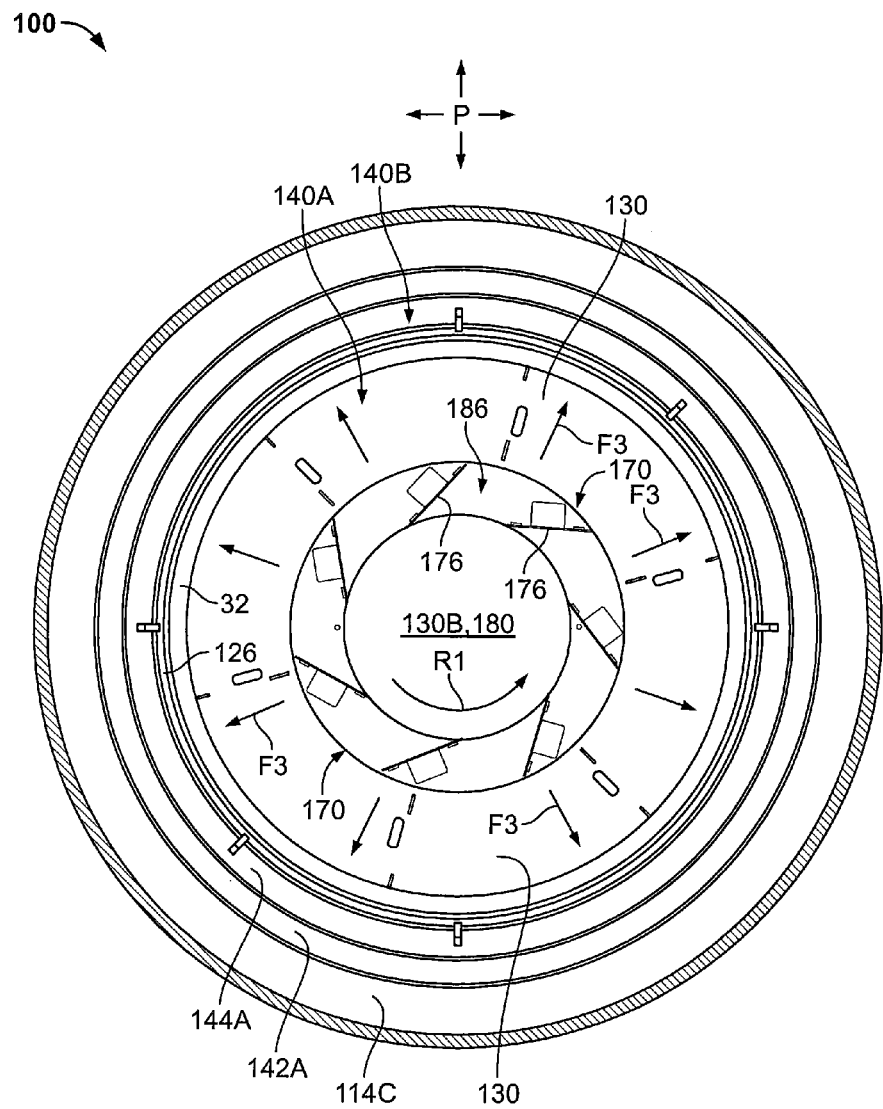
FIG. 10 is a cross-sectional view of the GC oven of FIG. 1 taken along the line 10-10 of FIG. 9, wherein the GC oven is operating in the cooling mode.

The rear baffle 132 defines an exhaust channel 142 between the rear side of the rear baffle 132 and the front side of the back end wall 114B. The edge 132C and the back side wall 114C define an annular entrance slot 142A fluidly connecting the chamber 140 and the exhaust channel 142 (FIGS. 9 and 10). The exhaust channel 142 fluidly communicates with the exhaust port 114A.

Figure 11:
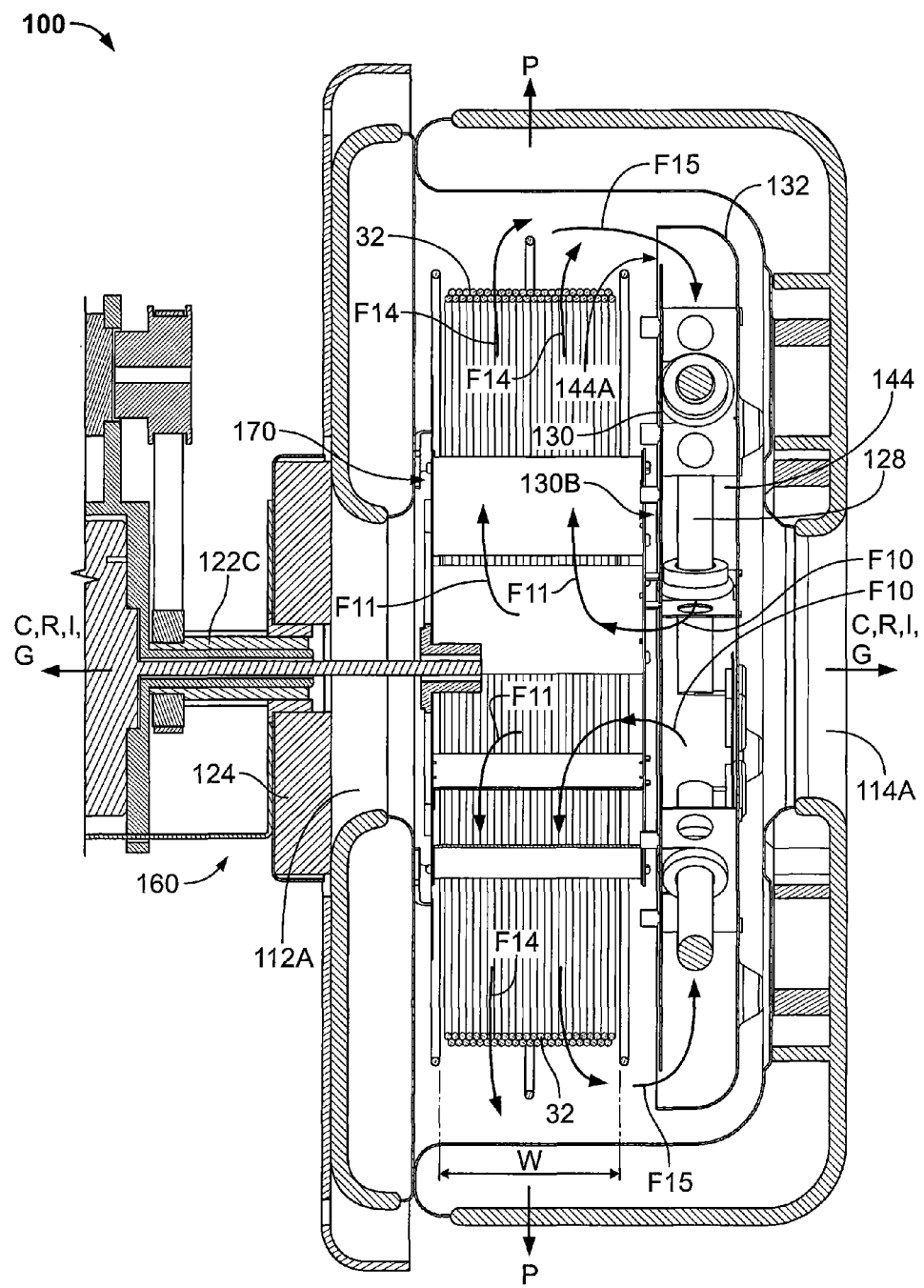
FIG. 11 is a fragmentary, cross-sectional view of the GC oven of FIG. 1 taken along the line 9-9 of FIG. 1, wherein the GC oven is operating in a recirculating mode.
Figure 12:
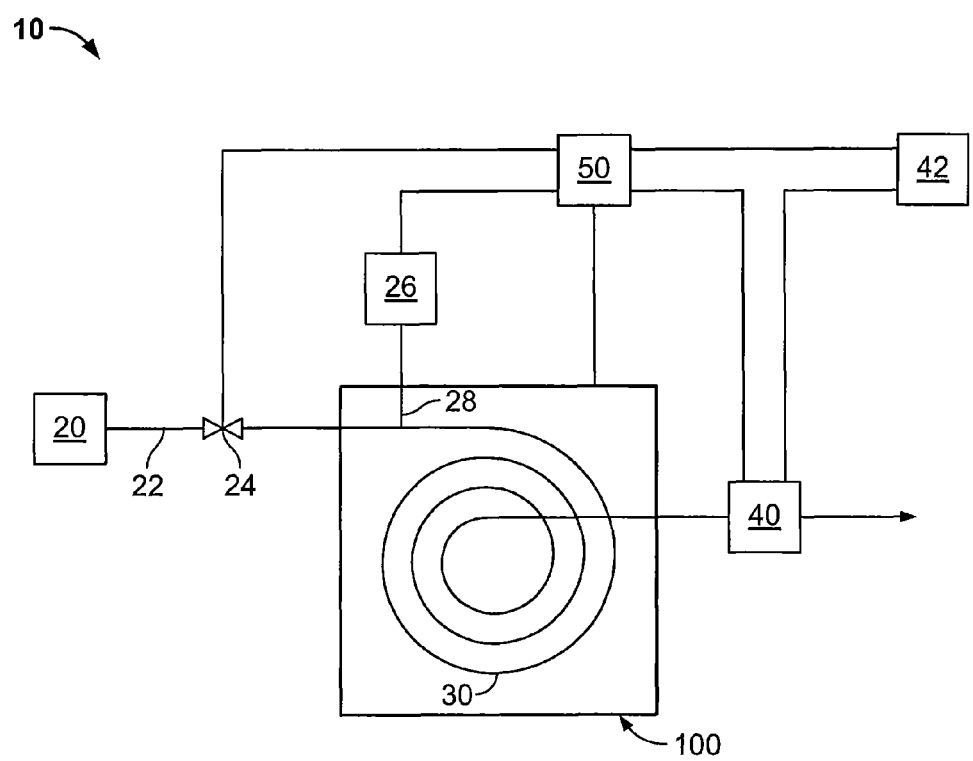
FIG. 12 is a schematic diagram showing a gas chromatography system including the GC oven of FIG. 1.

The front baffle 130 and the rear baffle 132 define a return channel 144 therebetween (FIG. 11). The peripheral edges 130A and 132C define an annular entrance slot 144A (FIGS. 10 and 11) fluidly connecting the chamber 140 with the return channel 144. The return channel 144 fluidly communicates with the return opening 130B. The heating element 128 is disposed in the return channel 130.

The fluid flow generating system 160 (FIG. 9) includes a motor (e.g., an electric motor) 162 and an impeller 170 mounted on an output shaft 162A of the motor 160 to be driven in a rotation direction R1 (FIG. 10) about an impeller rotation axis R-R. The motor 162 is mounted on the support brackets 116.

Figure 3:
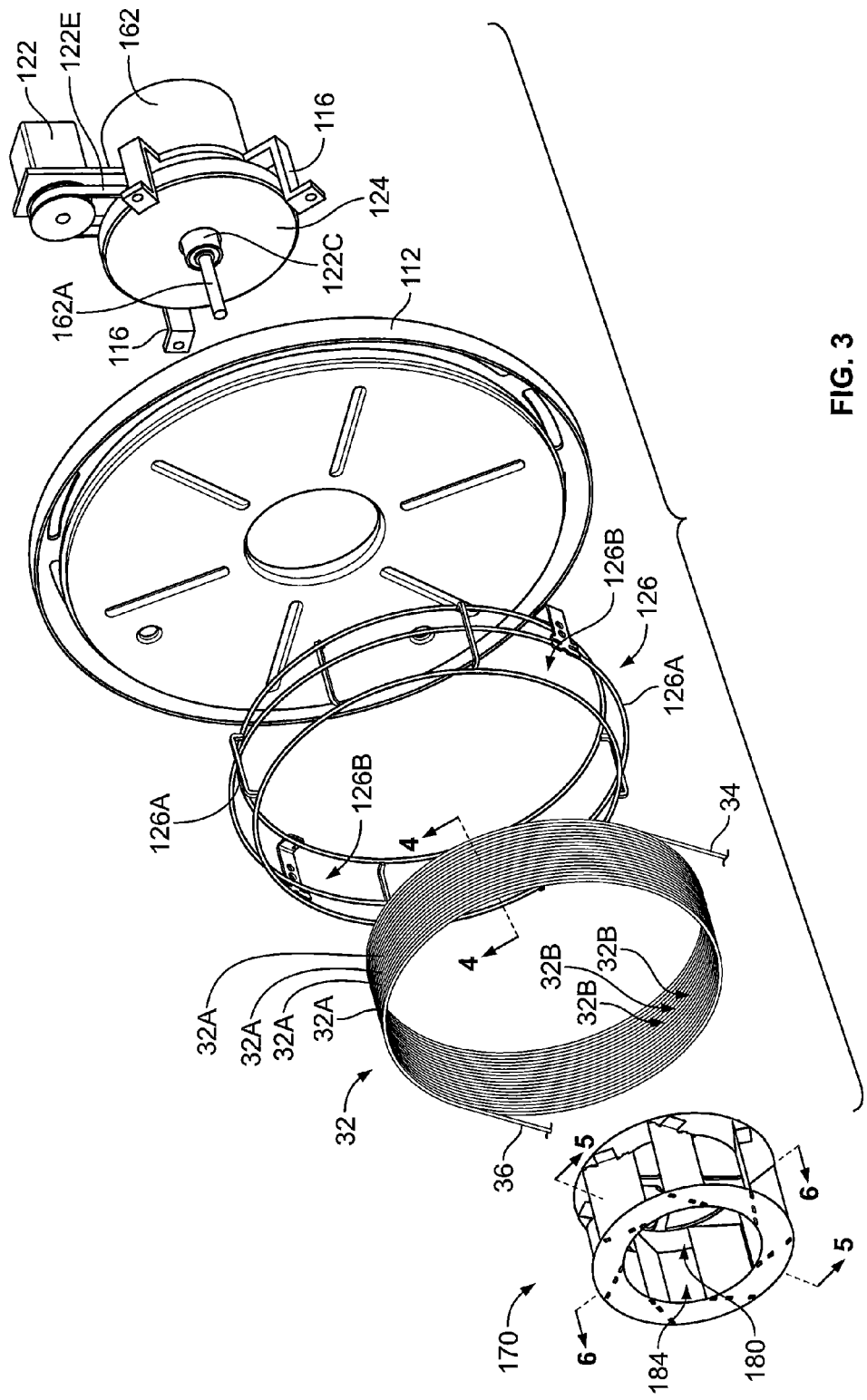
FIG. 3 is an exploded, rear perspective view of the lid assembly of FIG. 2.
Figure 4:
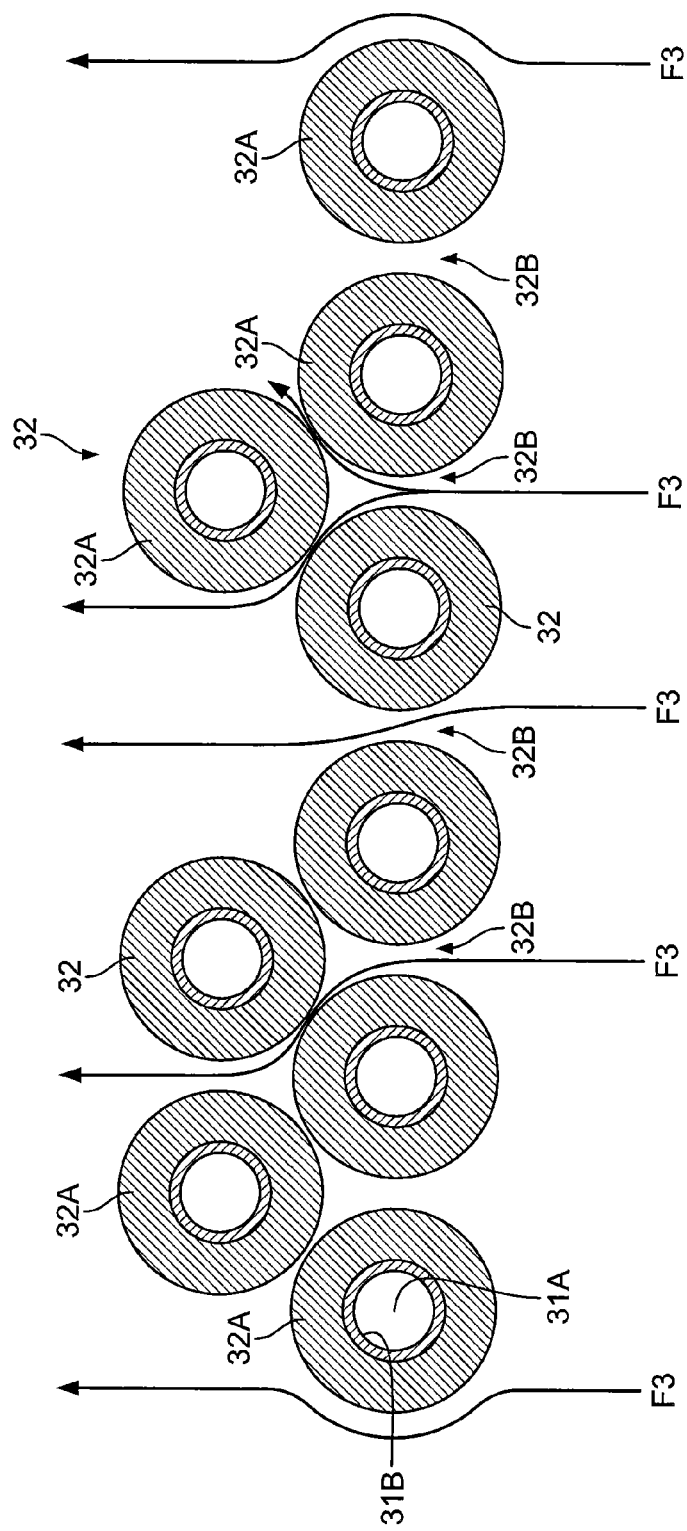
FIG. 4 is a cross-sectional view of a column forming a part of the GC oven of FIG. 1 taken along the line 4-4 of FIG. 3.
Figure 5:
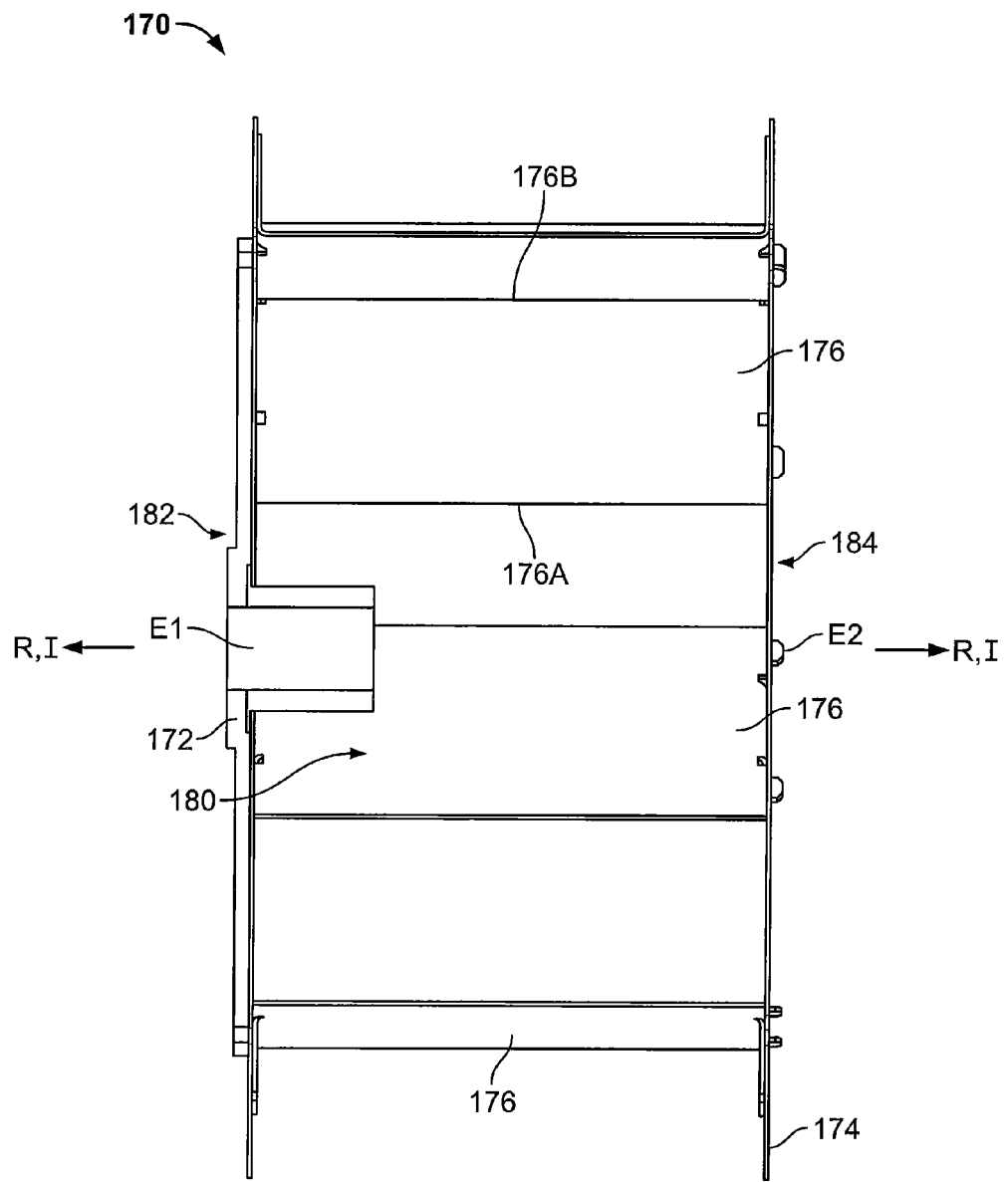
FIG. 5 is a cross-sectional view of an impeller forming a part of the GC oven of FIG. 1 taken along the line 5-5 of FIG. 3.
Figure 6:
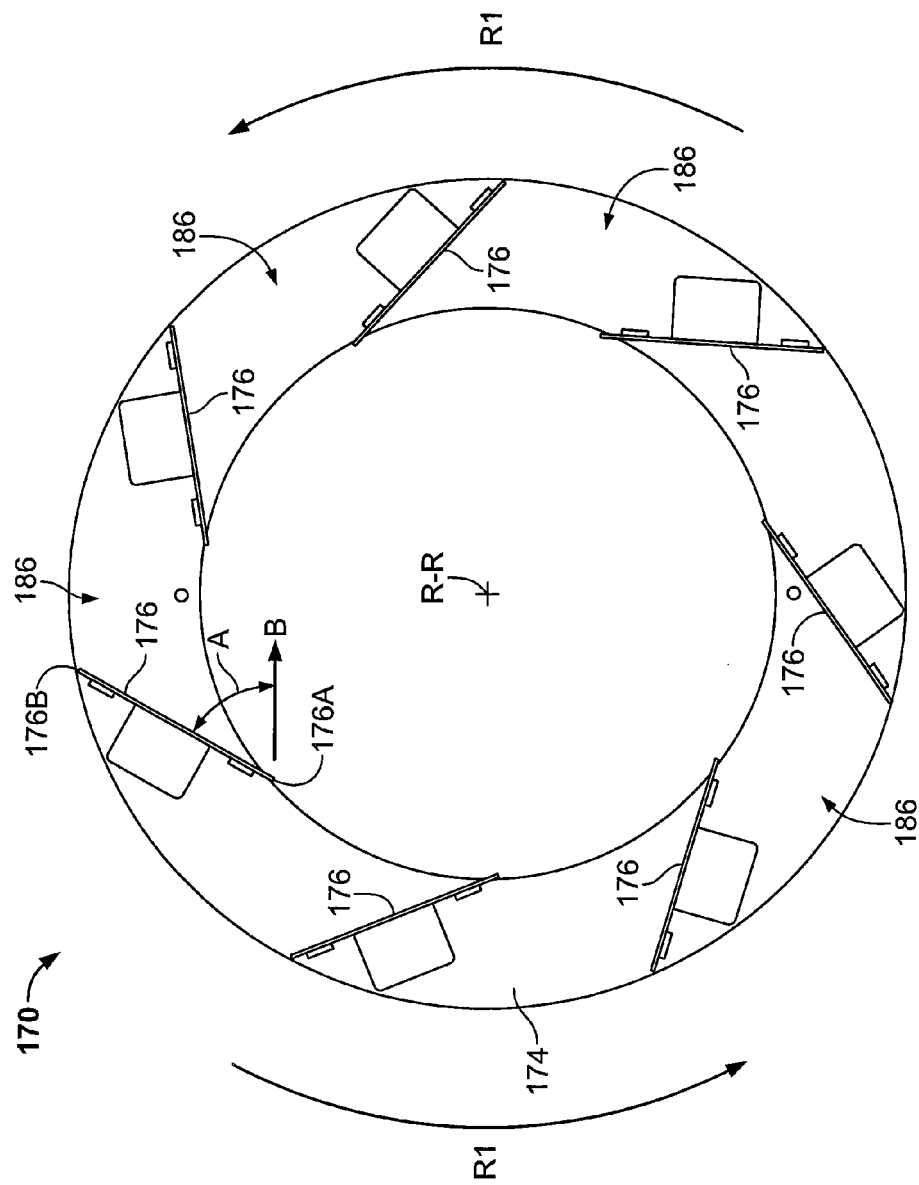
FIG. 6 is a cross-sectional view of the impeller of FIG. 5 taken along the line 6-6 of FIG. 3.

With reference to FIGS. 3, 5, and 6, the impeller 170 is a radial flow impeller configured to generate (when rotated in the direction R) a radially outward forced air flow F3 (FIGS. 4, 9 and 10). According to some embodiments and as shown, the impeller 170 is configured to generate a radially outward forced air flow that is substantially uniformly distributed about the full circumference (i.e., 360 degrees) of the impeller 170. According to some embodiments and as illustrated, the impeller 170 is a dual inlet (i.e., dual suction) centrifugal impeller with backward inclined blades and configured to generate axial-to-radially outward flow (i.e., with axial flow intakes and radial flow discharge).

Turning to the illustrated impeller 170 in more detail, the impeller 170 has a central impeller axis I-I coincident and concentric with the oven central axis C-C. The impeller 170 includes a hub 172, a support ring 174, and a plurality of vanes or blades 176 (as shown, seven) extending between and affixed at each end to the hub 172 and the support ring 174. The hub 172 is affixed to the end of the motor shaft 162A for rotation therewith. Each blade 176 has a leading edge 176A and a trailing edge 176B. According to some embodiments, each edge 176A, 176B extends linearly and substantially parallel to the impeller axis I-I.

A front impeller axial inlet 182 is defined in the hub 172. A rear impeller axial inlet 184 is defined in the ring 174 and is axially spaced apart from the inlet 182 along the axis I-I. The inlet 182 and the inlet 184 define an intake eye E1 and an intake eye E2, respectively, of the impeller 170. According to some embodiments, the intake eyes E1 and E2 are each located substantially on the impeller axis I-I. The impeller 170 (and in particular, the leading edges 176A of the blades 176) defines a through passage 180 terminating on each axial end thereof at the inlets 182, 184. According to some embodiments, the through passage 180 is substantially cylindrical and has a central axis substantially coincident and concentric with the impeller axis I-I. A radial slot 186 is defined between each adjacent pair of blades 176.

Each blade 176 is backward inclined to define an incline angle A with respect to the local rotational or tangential direction of travel B (i.e., to a circle centered about the axis R-R). According to some embodiments, the blades 176 are flat as shown. In other embodiments, the blades 176 are convexly curved.

The impeller 170 may be formed of any suitable material(s). According to some embodiments, the impeller 170 is formed of a rigid polymeric material or metal (e.g., stainless steel).

The impeller 170 is positioned in the chamber 140 such that the impeller 170 is concentric with the column loop 32 (i.e., the impeller axis I-I is coincident with the column axis G-G). According to some embodiments and as shown, the impeller 170 is located radially within the column loop 32 (i.e., the loop 32 defines a loop plane P-P and the impeller 170 also lies within the plane P-P). According to some embodiments and as shown, the loop plane P-P is substantially perpendicular to the impeller axis I-I. The loop 32 divides the chamber 140 into an annular inner region 140A (between the impeller 170 and the coil 32) and an annular outer region 140B (between the loop 32 and the side wall 114C). According to some embodiments, the side wall 114C and the regions 140A and 140B are each concentric with the impeller 170 and the loop 32. According to some embodiments, the front baffle opening 130B and the inlet port 112A are each concentric with the impeller 170. According to some embodiments, the entrance slot 142A and the return slot 144A are each concentric with the impeller 170. In some embodiments, the heating element 128 is concentric with the impeller 170. In some embodiments and as shown in the drawings, all of the foregoing components are concentric with the impeller 170 axis I-I.

The oven 100 can be used as follows in accordance with methods and operations of the present technology to dynamically control a temperature of the column loop 32. The activation/deactivation of the motors 122A, 162 as described herein may be executed by the controller 50 and/or another suitable controller and the operations may be executed programmatically or manually (e.g., fully automatically or semi-automatically). It will be appreciated that the GC system 10 may be otherwise operated as appropriate (e.g., in known or conventional manner) to provide a carrier gas flow through the column 30, inject the sample, analyze the exiting flow, etc., and that the oven 100 may be used to execute any suitable temperature program for the column loop 32 (e.g., isothermal or ramped).

In general, the oven 100 can operate in two alternative modes, a cooling mode and a recirculating mode. In the recirculating node, the oven 100 may use a recirculating forced air flow to convectively transfer heat energy from the heating element 128 to the column loop 32. In the cooling mode, the oven 100 may force a relatively cool flow of ambient air across the column loop 32 and out of the oven 100 to convectively cool the column loop 32.

With reference to FIGS. 9 and 10, the oven 100 is placed in the cooling mode by opening the door 124 (using the motor 122A) and forcibly rotating the impeller 170 in the rotation direction R1 (using the motor 162). The rotating impeller blades 176 generate a suction or negative pressure differential in the through passage 180 that draws an axial intake flow F1 of ambient air into the passage 180 through the inlet port 112A and the front inlet 182 and generally parallel to the rotation axis R-R as shown in FIG. 9. The blades 176 push and direct the air out of the passage 180 through the slots 186 (flow F2) in a radially outward direction at right angles to the rotation axis R-R as a radial flow F3 into the region 140A. The impeller 170 increases the pressure of the air above that of ambient so that the air flow F3 continues to flow radially through the column loop 32 (and thereby between and about the loop sections 32A through the voids 32B) into the region 140B. The air continues to flow as an air flow F5 into the exhaust channel 142 through the slot 142A, through the exhaust channel 142 and out of the housing 110 through the exhaust port 114A.

In some embodiments, the oven 100 is configured such that at least a majority of the air flow F3 passes through the exhaust slot 142A and the exhaust channel 142 to the exhaust port 114A as the air flow F5 rather than into the return slot 144A and channel 144 (i.e., the air flow F5 is the dominant air flow) and, in some embodiments, at least 90% of the air flow F3 follows this path. However, in some embodiments, a portion of the air flow F3 may enter the return channel 144 through the return slot 144A and be recirculated by the impeller 170.

With reference to FIG. 11, the oven 100 is placed in recirculating mode by closing the inlet port 112A with the door 124 and rotating the impeller 170 in the direction R1. The rotating impeller blades 176 generate a suction or negative pressure in the passage 180 that draws an axial intake flow F10 of air into the passage 180 through the rear inlet 184 from the return channel 144. The impeller blades 176 push and direct the air out of the passage 180 through the slots 186 (flow F11) in a radially outward direction at right angles to the axis R-R as a radial flow F14 into the region 140A. The impeller 170 increases the pressure of the air above that of the return channel 144 so that the air continues to flow radially through the loop 32 (between and about the loop section 32A) as an air flow F14 into the region 140B. The air continues to flow as an air flow F15 into the return channel 133 through the slot 144A, through the return channel 144, and back to the rear inlet 184 through the baffle opening 130B. The brackets 128A can serve to thermally insulate the heating element 128 from the baffle 130 and to inhibit swirling in the air flow F15. This flow path is recirculated repeatedly. As the air flow flows through the return channel 144 and over the heating element 128 therein, heat is convectively transferred from the heating element 128 to the air flow F15 and subsequently from the air flow F14 to the column loop sections 32A, thereby heating the loop sections 32A.

The oven 100 incorporates a high level of symmetry in the arrangement of the impeller 170, column loop 32, chamber 140 and other components. This in turn provides a high level of symmetry in the heat transfer fluid (air) flow path, and a corresponding high level of uniformity in convective heat transfer by the circulating air flow. In each of the cooling mode and the recirculating mode, the impeller 170 can provide a high velocity, high volumetric flow rate air flow over and through the column loop 32 substantially uniformly about 360 degrees from the column loop central axis G-G and radially outward. The impeller 170 and the configuration of the oven 100 can provide a turbulent air flow directly and uniformly onto and through the column loop 32 itself. The flow profile and the placement of the impeller 170 in the plane P-P of the column loop 32 can provide a circumferentially and axially uniform air flow profile with respect to the column loop 32, which in turn provides a more uniform and stable temperature profile across the loop 32 and throughout the column space (regions 140A, 140B). In this way, the oven 100 can reduce or minimize temperature gradients in the column loop 32 and thereby improve retention times and repeatability.

The impeller 170 can provide a high level of turbulence. The air flow mixing provided by this turbulence can also improve thermal uniformity in the air flow directed at the loop 32.

The radial symmetry of the heating element 128 and its concentricity with the impeller 170 may provide substantially uniform heat transfer from the heating element 128 and to the loop 32.

The arrangement of the oven 100, and in particular the placement of the impeller 170 within the loop 32 can enable an oven that is more compact and has lower thermal mass. The lower thermal mass can provide better thermal response to allow for faster heating and cooling cycles.

In order to provide the flows F3, F14 through the column loop 32, the impeller 170 must overcome the pressure drop across the loop 32. The backward inclined blades 176 may be beneficial in that blades so oriented can effectively overcome higher pressure differentials across the blades (e.g., due to upstream resistance or a densely packed loop 32).

According to some embodiments, an exhaust door may be provided to selectively open (in cooling mode) the exhaust port 114A and close (in recirculating mode) the exhaust port 114A.

According to some embodiments, the volumetric flow rate of the air flows F3, F14 through the column loop 32 is at least 20 CFM, in some embodiments, in the range of from about 20 to 100 CFM and, in some embodiments, from about 50 to 70 CFM.

Figure 13:
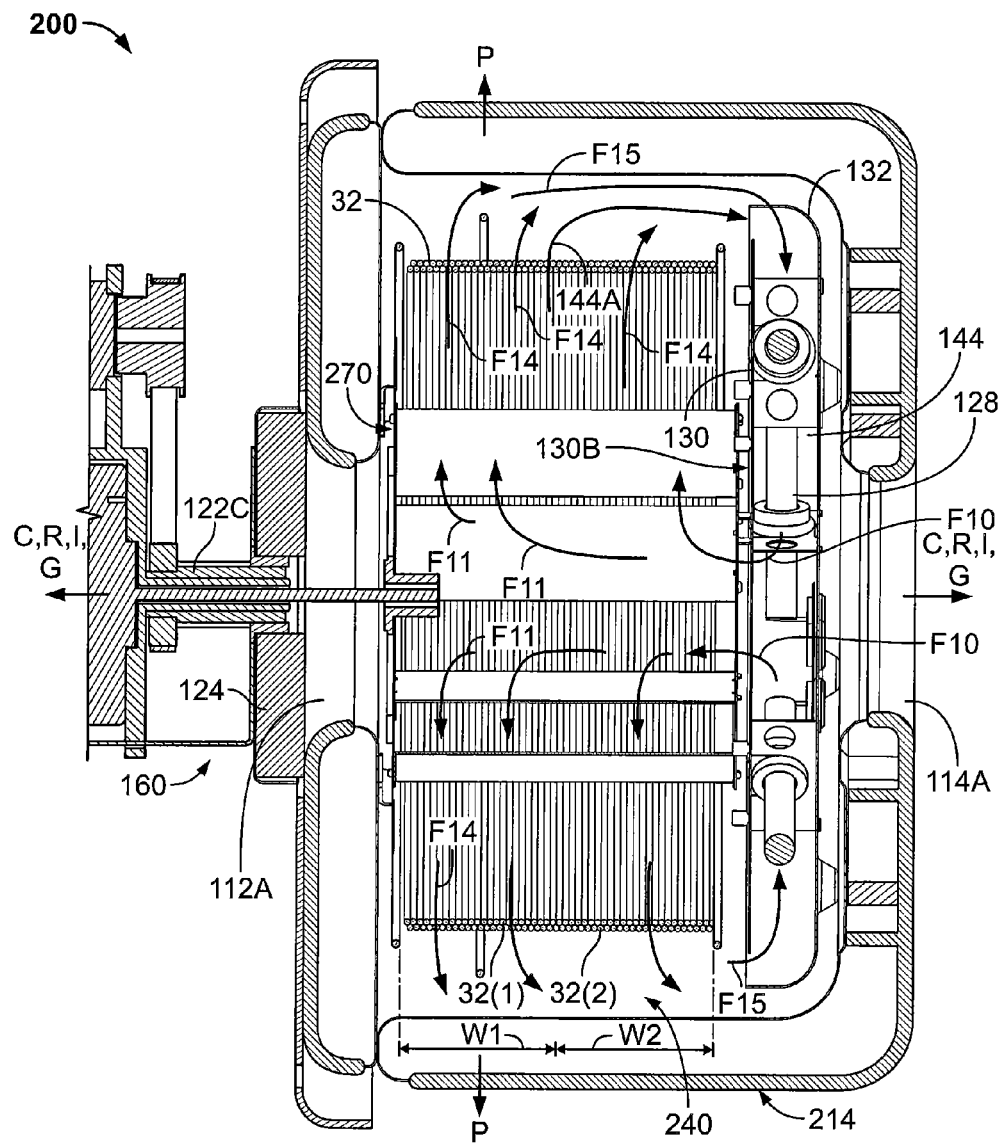
FIG. 13 is a cross-sectional view of a GC oven according to further embodiments of the technology.

With reference to FIG. 13, a GC oven 200 according to further embodiments is shown therein. The oven 200 is constructed and operated in the same manner as the oven 100, except as follows. In the oven 200, two separate column loops 32(1) and 32(2) are provided in place of the single column loop 32 on the impeller 270. The column loops 32(1) and 32(2) are mounted side-by-side and concentrically. The depth of the column chamber 240 and the width of the impeller 270 are increased to accommodate the combined widths W1 and W2 of the column loops 32(1) and 32(2). The column loops 32(1) and 32(2) may each correspond to and be constructed in the same manner as the column loop 32. The column loops 32(1), 32(2) may be configured and used in parallel with each column loop 32(1), 32(2) having its own feed and exit sections. The column loops 32(1), 32(2) may be heated and cooled in the same manner described above with regard to the oven 100. Further embodiments may be configured with three or more side-by-side independent column loops.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims, therefore, are to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

What is claimed:

1. A gas chromatography system comprising:
   a gas chromatography oven including:
      a housing defining an oven chamber and an intake port fluidly communicating with the oven chamber; and
      a fluid flow generating system including a radial flow impeller; and
   a gas chromatography column disposed in the oven chamber;
   wherein the oven is configured to selectively operate in each of:
      a cooling mode wherein the radial flow impeller generates a cooling fluid flow that is drawn from the intake port and flows about the column and out of the oven chamber; and alternatively
      a recirculating mode wherein the radial flow impeller generates a recirculating fluid flow within the oven chamber that repeatedly flows about the column and back to the radial flow impeller; and
   wherein:
      the oven includes at least one baffle in the oven chamber defining an exit channel and a return channel;
      the cooling fluid flow flows through the exit channel to the exhaust port;
      the recirculating fluid flow flows through the return channel to the radial flow impeller;
      in each of the cooling mode and the recirculating mode, the radial flow impeller discharges a forced fluid flow radially outwardly therefrom;
      the column is configured in a substantially circular column loop; and
      the radial flow impeller is located within the column loop so that the forced fluid flow is directed toward the column.

2. The gas chromatography system of claim 1 wherein:
   the oven includes a heating element; and
   in the recirculating mode, the recirculating fluid flow flows about the heating element and is heated thereby.

3. The gas chromatography system of claim 1 wherein:
   the oven includes an exhaust port; and
   in the cooling mode, the cooling fluid flow flows out of the housing through the exhaust port.

4. The gas chromatography system of claim 1 wherein:
   the oven includes a closure mechanism to selectively open and close the intake port;
   when the intake port is open, the oven operates in the cooling mode; and
   when the intake port is closed, the oven operates in the recirculating mode.

5. The gas chromatography system of claim 1 wherein:
   the radial flow impeller has first and second opposed axial inlets;
   in the cooling mode, the cooling fluid flow is drawn into the radial flow impeller through the first axial inlet; and in the recirculating mode, the recirculating fluid flow is drawn into the radial flow impeller through the second axial inlet.

6. The gas chromatography system of claim 1 wherein the forced fluid flow is substantially uniformly distributed about the full circumference of the radial flow impeller.

7. The gas chromatography system of claim 6 wherein:
the radial flow impeller rotates about an impeller axis; and
the column loop is centered about a column axis substantially concentric with the impeller axis and defines a column loop plane substantially perpendicular to the impeller axis.

8. The gas chromatography system of claim 1 wherein the radial flow impeller includes a plurality of backward inclined blades.

9. The gas chromatography system of claim 8 wherein the blades are convexly curved.

10. The gas chromatography system of claim 1 wherein:
the radial flow impeller rotates about an impeller axis and includes a plurality of blades; and
each of the blades extends substantially parallel to the impeller axis across its full width.

11. The gas chromatography system of claim 1 wherein, in the cooling mode, the cooling fluid flow is drawn from ambient air through the intake port.

12. The gas chromatography system of claim 1 wherein the cooling fluid flow and the recirculating fluid flow are each air flows.

13. A gas chromatography system comprising:
a gas chromatography oven including:
a housing defining an oven chamber and an intake port fluidly communicating with the oven chamber; and
a fluid flow generating system including a radial flow impeller; and
a gas chromatography column disposed in the oven chamber;
wherein the oven is configured to selectively operate in each of:
a cooling mode wherein the radial flow impeller generates a cooling fluid flow that is drawn from the intake port and flows about the column and out of the oven chamber; and alternatively
a recirculating mode wherein the radial flow impeller generates a recirculating fluid flow within the oven chamber that repeatedly flows about the column and back to the radial flow impeller; and
wherein:
the radial flow impeller rotates about an impeller axis;
the impeller axis extends through the intake port;
in each of the cooling mode and the recirculating mode, the radial flow impeller discharges a forced fluid flow radially outwardly therefrom;
the column is configured in a substantially circular column loop; and
the radial flow impeller is located within the column loop so that the forced fluid flow is directed toward the column.

14. The gas chromatography system of claim 13 wherein:
the radial flow impeller has first and second opposed axial inlets;
in the cooling mode, the cooling fluid flow is drawn into the radial flow impeller through the first axial inlet;
in the recirculating mode, the recirculating fluid flow is drawn into the radial flow impeller through the second axial inlet;
the impeller axis extends through each of the first and second axial inlets.

15. The gas chromatography system of claim 14 wherein:
the radial flow impeller defines a through passage terminating at the first and second axial inlets; and
the impeller axis, the intake port and the through passage are substantially concentric.

* * * * *